United States Patent [19]

Horii et al.

[11] 3,953,293

[45] Apr. 27, 1976

[54] PROCESS FOR THE PREPARATION OF XYLOSTASIN

[75] Inventors: Satoshi Horii, Osaka; Ikuo Nogami, Kyoto; Toru Hasegawa, Kawani; Masahiko Yoneda, Uozakinaka, all of Japan

[73] Assignee: Takeda Chemical Industries, Ltd., Osaka, Japan

[22] Filed: July 31, 1974

[21] Appl. No.: 493,619

Related U.S. Application Data

[62] Division of Ser. No. 362,504, May 21, 1973, abandoned.

[30] Foreign Application Priority Data

May 31, 1972  Japan.............................. 47-54581

[52] U.S. Cl. ................................ 195/96; 195/31 P
[51] Int. Cl.².......................................... C12D 9/20
[58] Field of Search ............ 195/96, 29, 31 R, 31 P; 260/210 AB

[56] References Cited
UNITED STATES PATENTS

| | | |
|---|---|---|
| 3,792,037 | 2/1974 | Kawaguchi et al. .......... 260/210 AB |
| 3,826,802 | 7/1974 | Kawaguchi et al. .................. 195/96 |

OTHER PUBLICATIONS

Omoto et al., Chemical Abstracts Vol. 76, No. 19, p. 361 Abstract No. 111624 v (1972).

*Primary Examiner*—A. Louis Monacell
*Assistant Examiner*—Thomas G. Wiseman
*Attorney, Agent, or Firm*—Wenderoth, Lind & Ponack

[57] ABSTRACT

A novel aminoglycoside antibiotic, xylostasin, of the nomenclature O-β-D-xylofuranosyl-(1 → 5)-O-[α-2,6-diamino-2,6-dideoxy-D-glucopyranosyl-(1 → 4)]-2-deoxystreptamine and its pharmaceutically acceptable acid salts which are effective against infections with bacteria, and a process for producing the antibiotic by cultivating a strain belonging to the genus Bacillus which is capable of producing the antibiotic.

5 Claims, No Drawings

PROCESS FOR THE PREPARATION OF XYLOSTASIN

This is a division of application Ser. No. 362,504, filed May 21, 1973, now abandoned.

This invention relates to a novel aminoglycoside antibiotic, xylostasin, of the nomenclature O-β-D-xylofuranosyl-(1⟶5)-O-[α-2,6-diamino-2,6-dideoxy-D-glucopyranosyl-(1⟶4)]-2-deoxystreptamine represented by the formula:

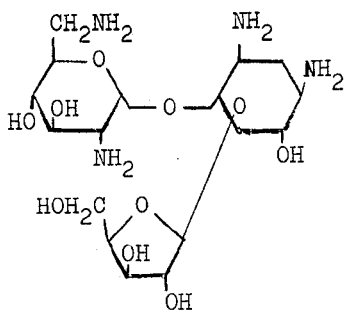

The present invention relates also to a novel and useful process for producing the antibiotic by cultivation of a microorganism of the genus Bacillus.

The principal object of the present invention is to provide xylostasin and its pharmaceutically acceptable acid salts.

The second object of the present invention is to provide a process for producing xylostasin and its pharmaceutically acceptable acid salts by cultivation of a microorganism of the genus Bacillus.

The principal object of the present invention is realized by cultivating a microorganism which belongs to the genus Bacillus and is capable of producing xylostasin in a culture medium containing assimilable carbon sources, digestible nitrogen sources and other nutrient factors necessary for the growth of the microorganism until xylostasin is accumulated and recovering the accumulated xylostasin from the culture broth.

The xylostasin-producing strain employable in the present invention may be any strain of the genus Bacillus that is capable of elaborating the desired antibiotic, and both spontaneous and induced mutants of such microorganisms can be employed. To ascertain if a microorganism is capable of elaborating xylostasin, one may follow the screening procedure described below, for instance.

Namely, glucose bouillon medium is inoculated with Bacillus strains isolated from the natural sources or such strains in stock cultures and the cultivation is carried out at 28°C for 3 to 4 days under shaking. After the resultant culture broth is confirmed to show antibacterial action against a suitable test organism such as *Bacillus subtilis*, *Escherichia coli* or *Staphylococcus aureus*, about 20 ml. of the culture filtrate is adjusted to pH 9–10 with alkali and, then, passed through a column of activated carbon (0.2 g.). After the column is washed with about 10 ml. of water, it is eluted with 10 ml. of 0.1—HCl. The eluate is neutralized and concentrated under reduced pressure. The concentrate is analyzed by paper electrophoresis on a filter paper, Whatman No. 1(W. & R. Balston Co. in U.S.A.), in borate buffer (pH 9.5; 0.025 M) at a voltage gradient of 2 KV/36 cm for 90 minutes. The spot of xylostasin can be detected by bioautography against a suitable organism such as *Bacillus subtilis* and can also be detected by color reaction using peptide reagent. Xylostasin is detected 5 to 6 cm to cathode.

The microorganisms employable in the present process are, for example, Bacillus sp. Y-399 and Bacillus sp. V-7, which are deposited under the following accession numbers.

Table 1

|  | ATCC | IFO |
|---|---|---|
| Bacillus sp. Y-399 | 21932 | 13321 |
| Bacillus sp. V-7 | 21933 | 13320 |

Remarks:

ATCC: "American Type Culture Collection" in Maryland, U.S.A.

IFO: "Institute for Fermentation, Osaka" in Osaka, Japan.

Bacillus sp. Y-399 was isolated by the present inventors from the soil of Kyoto, Japan and Bacillus sp. V-7 was isolated by the present inventors from the soil of Tokyo, Japan. These microorganisms have the microbiological characteristics as described in the Table. 2.

Table 2

| Characteristic | Bacillus sp. Y-399 | Bacillus sp. V-7 |
|---|---|---|
| (a) Appearance | | |
| 1) Shape and size | Rods, 0.8 by 2.4 to 3.4 μ, with rounded ends | Rods, 0.8 by 2.4 to 3.4 μ, with rounded ends |
| 2) Pleomorphism | Occurring singly, in pairs | Occurring singly, occasionally in pairs |
| 3) Motility and Flagellum | Motile, possessing peritrichous | Motile, possessing peritrichous |
| 4) Sporogenesis | Spores ellipsoidal or cylindrical, central to subterminal. Sporangia swollen and clavate. | Spores elipsoidal or cylindrical, terminal to subterminal. Sporangia swollen and clavate. |
| 5) Gram stain | Variable | Variable |
| 6) Acid-fastness | Non-acid-fast | Non-acid-fast |
| (b) Growth Characteristics | | |
| 1) Bouillon agar plate | Spreading, smooth, flat surface; entire; translucent, yellow and mucoid; | Spreading, smooth, flat surface; glistening, entire, translucent, grayish |

Table 2-continued

| Characteristic | Bacillus sp. Y-399 | Bacillus sp. V-7 |
|---|---|---|
| | micro-colonies are mobile | white and mucoid; mobile |
| 2) Bouillon agar slant | Moderate growth, rhizoid, flat, glistening, translucent and higly mucoid | Moderate growth, rhizoid, flat, glistening, grayish white and highly mucoid |
| 3) Bouillon | Moderate growth, no surface growth, turbid; cells are yellow | Moderate growth, no surface growth, turbid, cells are grayish white |
| 4) Potato | Moderate growth, spreading bright-yellow | Good growth, spreading, grayish-white |
| 5) Litmus milk | Neutral, peptonized and reduced | Reduced |
| (c) Physiological characteristics | | |
| 1) Nitrates reduction | Not reduced | Not reduced |
| 2) Denitration | Negative | |
| 3) MR test | Negative | Negative |
| 4) VP test | Negative | Negative |
| 5) Indole production | Not produced | Not produced |
| 6) Hydrogen sulfide production | Produced | Produced |
| 7) Starch hydrolysis | Weakly hydrolyzed | Weakly hydrolyzed |
| 8) Citrate utilization | Not utilized | Not utilized |
| 9) Nitrates utilization | Not utilized | Not utilized |
| 10) Ammonium utilization | Not utilized | Utilized |
| 11) Production of pigment | A water-insoluble yellow pigment (carotinoid) is intracellularly produced | Not produced |
| 12) Urease activity | Negative | Negative |
| 13) Cytochrome oxidase | Substantially absent | Present |
| 14) Methylene blue reduction | Reduced | Reduced |
| 15) Casein hydrolysis | Positive | Negative |
| 16) Gelatin liquefaction | Liquefied | Liquefied |
| 17) Growth pH | Growth at pH6–9; optimum growth at pH8 | Growth at pH6–9; optimum growth at pH8 |
| 18) Growth temperature | Growth at 15°–35°; optimum growth at 30° | Growth at 15°–45°; optimum growth at 30°–37° |
| 19) $O_2$ relation | Aerobic; no anaerobic growth in glucose bouillon | Aerobic; no anaerobic growth in glucose bouillon |
| 20) Resistance to sodium chloride | No growth at 5 % concentration | No growth at 5 % concentration |
| 21) O-F test | Neither acid nor gas is produced from D-glucose or from maltose | Neither acid nor gas is produced from D-glucose |
| 22) Catalase | Weak | Weak |

| (d) Carbohydrate fermentation | Acid | Gas | Acid | Gas |
|---|---|---|---|---|
| L-Arabinose | − | − | − | − |
| D-Xylose | − | − | − | − |
| D-Glucose | − | − | ± | − |
| D-Mannose | + | − | ++ | − |
| D-Fructose | − | − | + | − |
| D-Galactose | − | − | − | − |
| Maltose | ± | − | ++ | − |
| Sucrose | − | − | + | − |
| Lactose | − | − | − | − |
| Trehalose | + | − | + | − |
| D-Sorbitol | − | − | − | − |
| D-Mannitol | − | − | − | − |
| Inositol | − | − | − | − |
| Glycerin | − | − | − | − |
| Starch | + | − | ++ | − |

Comparison of the above microbiological characters with the corresponding entries in Bergey's Manual of Determinative Bacteriology (7th Edition) suggests that Bacillus sp. V-7 either belongs to *Bacillus circulans* or is a strain which is closely related to *Bacillus circulans*. ON the other hand, Bacillus sp. Y-399 cannot be identified with any of the microorganisms described in the above literature but rather bears a close resemblance to the IFO-13296 strain described in the specification of Japanese Patent Application No.98875/1971 and, therefore, is considered to belong to *Bacillus vitellinus*.

The method of this invention is practiced by cultivating said xylostasin-producing strain in a suitable medium. The medium may be one of those which are routinely used in the cultivation of microorganisms of the genus Bacillus. Thus, the medium may contain, as carbon sources, such carbohydrates as glucose, starch, dextrin, etc. and, as nitrogen sources, various organic and inorganic nitrogenous matters such as ammonium sulfate, ammonium chloride, amino acids, proteinous materials, etc., and these medium ingredients may be used either singly or in a suitable combination. In addition to these ingredients, the medium may further contain such inorganic matters as potassium, sodium, magnesium, iron, phosphoric acid, etc. and such growth promoting factors as vitamins, meat extract, yeast extract, peptone, organic acids, etc. The microorganism may be cultivated under stationary conditions but, generally, is preferably incubated under shaking or under aeration and stirring. The incubation temperature generally lies somewhere between 20° and 37°C and the incubation time may range from about 24 to 90 hours. It should be noticed that the optimum conditions are dependent upon, and should be selected with reference to, the characters of the particular xylostasin-producing strain to be employed.

When a xylostasin-producing Bacillus is thus cultivated under the conditions described above, xylostasin is predominantly produced in the culture filtrate. As will be seen from its physicochemical properties which will be described below, xylostasin in a water-soluble basic antibiotic, and, therefore, can be isolated by the general procedures for isolation of conventional water-soluble basic antibiotics including neomycin, paromomycin, kanamycin and the like.

Thus, to harvest xylostasin one may follow the procedure of passing the culture fluid over an adsorbent and desorbing the active compound with a suitable eluant or, alternatively, extract the antibiotic with a suitable solvent, though the former procedure is more desirable. More particularly, when the culture fluid is to be purified using activated carbon as an adsorbent, xylostasin is ready to be adsorbed on the alkaline side and, as to the eluant, it is advantageous to employ an aqueous solution which has been adjusted to a pH below 5 and, preferably, not exceeding 4, or such a solvent as aqueous acetone or aqueous alcohol. Xylostasin may also be purified by using an ion exchanger as the adsorbent. As an ion exchange resin, a cation exchange resin such as Amberlite IRC-50 (Rohm and Haas Co.) may be employed. As an eluent, an aqueous solution of acid, alkali or a salt is generally employed.

The crude powder of xylostasin which has been obtained in the above manner can be further purified by ion exchange chromatography on, for example, Dowex 1 × 2(OH⁻ form)(Dow Chemical Co.), Amberlite CG-50 (NH$_4^+$ - form) (Rohm and Haas Co.), CM-Sephadex (NH$_4^+$ form) (Pharmacia Fine Chemicals, Sweden) and the like. From the eluate obtained in the purification procedure using such an adsorbent, xylostasin is isolated, for instance, by concentrating the eluate to dryness, preferably at a lower temperature, or by adding a water-miscible organic solvent to the eluate and collecting the precipitates. Xylostasin is isolated in the form of an acid salt when the eluate is neutralized with an acid prior to or after concentration.

Xylostasin can be bioassayed by procedures which are conventional per se, e.g. by the paper disc method using *Bacillus subtilis* PCI 219 as a test organism.

The physicochemical and biological properties of the present antibiotic are as follows.

1. Xylostasin is a basic substance. Xylostasin, its hydrochloride and sulfate are all white crystalline powders. Xylostasin is stable in neutral or alkaline solution, but less stable in acidic solution.

2. Xylostasin does not give a definite melting point, decomposing with foaming in the region of about 150°–180°C.

3. Xylostasin is readily soluble in water and is slightly soluble in methanol, but is insoluble in such organic solvents as acetone, butanol, ethyl acetate, benzene, hexane, ether, etc.

4. The ultraviolet absorption spectrum of xylostasin shows no characteristic absorption except end absorption.

5. The infrared absorption spectrum of xylostasin in potassium bromide shows absorption bands characteristic of aminoglucoside antibiotics in the neighborhood of 3320, 2920, 1590, 1465, 1340, 1100 and 1020 cm⁻¹. However, since there is no absorption in the vicinity of 1652 cm⁻¹, it is evident that the molecule of xylostasin contains no acid amide bond.

6. The NMR spectrum (in D$_2$O) of xylostasin shows the following characteristic peaks.

$\delta$ values: 1.36 (q, 1H, axial methylene proton), 2.13 (m, 1H, equatorial methylene proton), 5.44(1H, J= <1, xylose anomeric proton), 5.70 (d, 1H, J=3 – 4, neosamine C anomeric proton).

7. The optical rotation of xylostasin as measured in aqueous solution: $[\alpha]_D^{23} + 34°$.

8. Color reactions. Xylostasin gives positive reactions in ninhydrin, molisch, anthrone and Greig - Leaback tests and negative reactions in Sakaguchi, maltol, ferric chloride, biuret and Ehrlich tests.

9. The elemental analysis and molecular weight found for a xylostasin sample which has been dried over phosphoric anhydride under reduced pressure at 110°C for 20 hours are: C, 44.18%; H, 7.58%; N, 11.98% and mol. wt.(neutralization equivalent) = 451.

The molecular formula postulated from structural studies: $C_{17}H_{34}N_4O_{10}$(calcd.: C, 44.93%; H, 7.54%; N, 12.33%; mol. wt. 454.49).

10. Xylostasin migrates about 5 to 6 cm to cathode in paper electrophoresis [borate buffer (pH 9.5; 0.025 M) on Whatman No.1 paper at 2 KV/36cm for 90 minutes].

11. When xylostasin is subjected to methanolysis with 0.4N HCl in methanol at 22°C for 6 days, methyl D-xyloside and neamine are produced and, when xylostasin is hydrolyzed with 0.5N sulfuric acid at 90°C for 6 hours, D-xylose and neamine are detected in the hydrolyzate.

12. The antimicrobial spectrum of xylostasin is shown in Table 3.

Table 3

Minimal inhibitory concentrations by the agar dilution method

| Test organisms | Minimal inhibitory concentration, mcg/ml |
|---|---|
| Escherichia coli IFO 3044 | 6.25 |
| Shigella flexneri EW-10 | 12.5 |
| Proteus vulgaris IFO 3045 | 50 |
| Pseudomonas aeruginosa IFO 3080 | >50 |
| Staphylococcus aureus FDA 209P | 6.25 |
| Bacillus subtilis PCI 219 | 3.125 |
| Bacillus cereus IFO 3466 | 50 |
| Bacillus brevis IFO 3331 | 25 |
| Sarcina lutea IFO 3232 | 25 |
| Mycobacterium avium IFO 3153 | 1.6 |
| Mycobacterium avium (Streptomycin-resistant) | 3.125 |
| Mycobacterium avium (Neomycin-resistant) | >50 |
| Mycobacterium phlei IFO 3158 | 1.6 |
| Mycobacterium smegmatis IFO 3083 | 1.6 |

Remarks:

FDA: "Food and Drug Administration" in Washington, D.C., U.S.A.

PCI: "Penicillin Control and Immunology Section, Food and Drug Administration" in Washington, D.C., U.S.A.

The media used for the test are bouillon agar for the common bacteria and glycerin bouillon agar for acid fast bacteria.

13. Acute toxicity:

The acute toxicity of xylostasin was examined by intravenous injection into mice. The $LD_{50}$ value for the free base was approximately 1,000 mg/kg.

14. An anti-infection test in mice:

When an aqueous solution of xylostasin was administered subcutaneously to mice, immediately after being infected with Escherichia coli 0-111, at a single dose of 10 mg/kg., the death of the mice was completely prevented.

Xylostasin and its pharmaceutically acceptable acid salts are effective against infections with bacteria and their toxicity is extremely low against animals (e.g. human, mouse, rat, etc.). Therefore, they are safely and effectively employable for the treatment of bacterial infections such as urinary tract infections, bronchopneumonia, pyelitis and angina tonsillaris. The present antibiotic can be administered parenterally in general, but can also be administered non-parenterally. The dosage should suitably be determined depending upon the symptoms of the disease to be treated and is selected from a range, for instance, from about 10 mg. to about 40 mg./kg. of body weight in every administration. The present antibiotic can be administered in per se conventional dosage forms such as injection, tablets and ointment.

EXAMPLE 1

A liquid medium (pH 7.2) containing 3% of polypeptone, 1% of meat extract, and 0.5% of sodium chloride is inoculated with Bacillus sp. Y-399 grown on a glycerin-bouillon-agar, and the cultivation was carried out under shaking at 28°C for 40 hours. This seed culture was then inoculated to a fermentation medium (30 l, pH 7.5) which comprises 1% of glucose, 1% of polypeptone, 0.7% of meat extract and 0.5% of magnesium chloride in a 50 l tank at an inoculum size of 10% and the cultivation was carried out at 28°C, 100% aeration and 200 r.p.m. for 66 hours.

The resultant fermentation broth was adjusted to pH 1–2 with a saturated aqueous solution of oxalic acid and, then, filtered with a filter aid[300 g. Hyflo-Super-Cel(Johns-Manville Products Co.)]. The filtrate was adjusted to pH 7 and passed through a column packed with 2 l of cation exchange resin [Amberlite IRC-50 ($NH_4^+$ form)], whereupon the active product was adsorbed on the ion exchange resin. The resin was first washed with water and, then, eluted with 5% aqueous ammonia. The active fractions (2,5 l) were pooled and run onto a column of 600 ml of a chromatographic grade of activated carbon to absorb the active compound. The carbon column was washed with water and, then, eluted with an 0.3N aqueous solution of HCl. The active fractions were pooled, neutralized with anion exchange resin [Amberlite IR 45 (Rohm and Haas Co., $OH^-$ form)] and concentrated under reduced pressure. Finally, the concentrate was lyophilized to obtain 5.6 g. of a crude powder containing about 30% of xylostasin.

Purification procedure

The crude product (9.6 g) obtained as in the above procedure was dissolved in water and adsorbed on a column of 150 ml of cation exchange resin [Amberlite CG-50(Rohm and Haas Co., $NH_4^+$ form)]. After washing with water, the column was eluted with 0.2N ammonia water. The active fractions were collected and concentrated under reduced pressure. Acetone was added to the concentrate and the resultant precipitates were collected by filtration. The procedure yielded 3.0 g. of a pale-yellow powder (xylostasin content: about 90%). This powder was dissolved in water and adsorbed on a column (3 cm × 90cm) of cation exchanger[CM-Sephadex C-25 ($NH_4^+$ form)]. The column was then eluted with aqueous ammonia using the technique of gradient elution (from 0 to 1.7N) and the active fractions containing xylostasin alone were pooled and concentrated to dryness under reduced pressure, whereupon 2.4 g. of a white xylostasin powder was obtained.

Preparation of sulfate

An aqueous solution of the xylostasin (free base) as obtained above was adjusted to pH 4–5 with 2N-sulfuric acid and run onto a column of activated carbon. The column was eluted with 0.03N-sulfuric acid and the active fractions were pooled, adjusted to pH 6.0 with anion exchange resin[Amberlite IR-45 ($OH^-$ form)] and concentrated under reduced pressure.

Acetone was added to the concentrate and the resultant precipitate was harvested by filtration and dried under reduced pressure. The procedure yielded white powder of xylostasin sulfate.

EXAMPLE 2

A liquid medium (pH 7.2) containing 3% of polypeptone, 1% of meat extract and 0.5% of sodium chloride was inoculated with Bacillus sp. V-7 grown on a glycerin-bouillon-agar slant and the cultivation was carried out under shaking at 28°C for 40 hours. The resultant seed culture was then inoculated into a 50 l tank containing 30 l of a fermentation medium (pH 8.0) which comprises 1% of glucose, 0.7% of polypeptone, 0.5% of meat extract and 0.3% of sodium chloride at an inoculum size of 10% and the fermentation was carried out at 28°C, 100% aeration and 200 r.p.m. for 66 hours.

To the resultant fermentation broth, there were added 150 ml of a 4% aqueous solution of agglutinant

[Primafloc C-7 (Rohm and Haas Co.)] and 300 g. of filter aid [Hyflo-Super-Cel (Johns-Manville Products Co.)].

The mixture was adjusted to pH 1 - 2 with a saturated aqueous solution of oxalic acid and filtered. The filtrate (24 l) was adjusted to pH 8.5 - 9.5 and stirred with about 1% of activated carbon for 30 minutes, whereby the active substance in the filtrate was almost exclusively adsorbed on the carbon. The carbon was taken up, washed with water and suspended in 3 l of 70% methanol in water. Then, the suspension was brought to pH 2 with 4N-hydrochloric acid to extract the active substance and the carbon was filtered off. The filtrate was concentrated under reduced pressure to distill the methanol off and, then, neutralized with anion exchange resin [Amberlite IR-45(OH$^-$ form)]. The solution was adjusted to pH 7 and then run onto a column of cation exchange resin [Amberlite CG-50 (NH$_4^+$ form)], whereby the active substance was adsorbed. The column was eluted with aqueous ammonia using the technique of gradient elution (from 0 to 10% concentration).

The active fractions were collected and concentrated under reduced pressure, followed by the addition of acetone. The procedure yielded about 5.7 g. of crude xylostasin (xylostasin content: about 30%).

Purification procedure

The crude product (9.6 g.) as obtained above was subjected to a treatment similar to that as in Example 1, whereupon 2.5 g. of white powder of xylostasin is obtained.

EXAMPLE 3

A liquid culture medium (pH 7.2) containing 3% of polypeptone, 1% of meat extract and 0.5% of sodium chloride was inoculated with Bacillus sp. Y-399 grown on a glucose bouillon agar slant, and incubated for 40 hours at 28°C under shaking.

The seed culture was used to inoculate 30 l of fermentation medium (pH 7.5) containing 2% of dextrin, 0.5% of soluble starch, 1.2% of polypeptone, 0.7 % of meat extract and 0.5% of magnesium sulfate in 50 l fermentor at the inoculum size of 10% and the cultivation was conducted at 28°C, 100% aeration and 200 r.p.m. The resulting culture broth was treated in a manner similar to that as in Example 1, whereby 22.1 g. of crude powder containing about 70% of xylostasin is obtained.

What we claim is:

1. A process for producing O-$\beta$-D-xylofuranosyl-(1⟶5)-O-[$\alpha$-2,6-diamino-2,6-dideoxy-D-glucopyranosyl-(1⟶4)]2-deoxystreptamine of a pharmaceutically acceptable acid salt thereof, which comprises cultivating a microorganism belonging to the genus Bacillus, which is capable of producing the antibiotic, in a culture medium containing assimilable carbon sources, digestible nitrogen sources and other nutrient sources necessary for the growth of the microorganism until the antibiotic is accumulated in the culture broth, and recovering the antibiotic from the culture broth.

2. The process as claimed in claim 1, wherein the microorganism is *Bacillus circulans*.

3. The process as claimed in claim 1, wherein the microorganism is *Bacillus vitellinus*.

4. The process as claimed in claim 1, wherein the microorganism is Bacillus sp. Y-399 (ATCC-21932).

5. The process as claimed in the claim 1, wherein the microorganism is Bacillus sp. V-7 (ATCC-21933).

* * * * *